(12) United States Patent
Bui-Khac et al.

(10) Patent No.: US 6,759,539 B1
(45) Date of Patent: Jul. 6, 2004

(54) PROCESS FOR ISOLATION AND PURIFICATION OF PACLITAXEL FROM NATURAL SOURCES

(75) Inventors: Trung Bui-Khac, Montreal (CA); Michel Potier, Montreal (CA)

(73) Assignee: Chaichem Pharmaceuticals International, Laval (CA)

( * ) Notice: Subject to any disclaimer, the term of this patent is extended or adjusted under 35 U.S.C. 154(b) by 0 days.

(21) Appl. No.: 10/375,474

(22) Filed: Feb. 27, 2003

(51) Int. Cl.$^7$ ............................................. C07D 305/14
(52) U.S. Cl. ........................ 549/510; 549/511; 435/123
(58) Field of Search .............................. 549/510, 511; 435/123

(56) References Cited

U.S. PATENT DOCUMENTS

| | | | |
|---|---|---|---|
| 4,857,653 A | 8/1989 | Colin et al. | |
| 4,924,011 A | 5/1990 | Denis et al. | |
| 5,015,744 A | 5/1991 | Holton | |
| 5,019,504 A | 5/1991 | Christen et al. | |
| 5,175,315 A | 12/1992 | Holton | |
| 5,200,534 A | 4/1993 | Rao | |
| 5,279,949 A * | 1/1994 | Nair | 435/123 |
| 5,312,740 A | 5/1994 | Saito et al. | |
| 5,322,779 A | 6/1994 | Strobel et al. | |
| 5,336,785 A | 8/1994 | Holton | |
| 5,367,086 A | 11/1994 | Rao | |
| 5,380,916 A | 1/1995 | Rao | |
| 5,384,399 A | 1/1995 | Holton | |
| 5,405,972 A | 4/1995 | Holton et al. | |
| 5,440,055 A | 8/1995 | Castor | |
| 5,445,809 A | 8/1995 | Strobel | |
| 5,451,392 A | 9/1995 | Strobel et al. | |
| 5,470,866 A | 11/1995 | Kingston et al. | |
| 5,475,120 A | 12/1995 | Rao | |
| 5,478,736 A * | 12/1995 | Nair | 435/123 |
| 5,480,639 A | 1/1996 | ElSohly et al. | |
| 5,508,447 A | 4/1996 | Magnus | |
| 5,516,676 A | 5/1996 | Hanson et al. | |
| 5,530,020 A | 6/1996 | Gunawardana et al. | |
| 5,594,157 A | 1/1997 | Gunawardana et al. | |
| 5,614,645 A | 3/1997 | Kingston et al. | |
| 5,616,330 A | 4/1997 | Kaufman et al. | |
| 5,618,538 A | 4/1997 | ElSohly et al. | |
| 5,618,952 A | 4/1997 | Holton et al. | |
| 5,637,484 A | 6/1997 | Yukimune et al. | |
| 5,654,448 A | 8/1997 | Pandey et al. | |
| 5,665,576 A | 9/1997 | Cino et al. | |
| 5,670,673 A | 9/1997 | Rao | |
| 5,675,025 A | 10/1997 | Sisti et al. | |
| 5,679,807 A | 10/1997 | Murray et al. | |
| 5,684,169 A | 11/1997 | Hamada et al. | |
| 5,693,666 A | 12/1997 | Chen et al. | |
| 5,703,247 A | 12/1997 | Kingston et al. | |
| 5,719,265 A | 2/1998 | Mongelli et al. | |
| 5,739,016 A | 4/1998 | Hanson et al. | |
| 5,739,359 A | 4/1998 | Kingston et al. | |
| 5,744,333 A | 4/1998 | Cociancich et al. | |
| 5,750,737 A | 5/1998 | Sisti et al. | |
| 5,756,536 A | 5/1998 | Chen et al. | |
| 5,760,251 A | 6/1998 | Gao et al. | |
| 5,760,252 A | 6/1998 | Holton et al. | |
| 5,767,297 A | 6/1998 | Mandai et al. | |
| 5,770,745 A | 6/1998 | Swindell et al. | |
| 5,773,629 A | 6/1998 | Yang et al. | |
| 5,780,653 A | 7/1998 | Tao et al. | |
| 5,795,909 A | 8/1998 | Shashoua et al. | |
| 5,969,165 A | 10/1999 | Liu | |
| 6,452,024 B1 * | 9/2002 | Bui-Khac et al. | 549/510 |

FOREIGN PATENT DOCUMENTS

CA          2072400 A1      1/1993

OTHER PUBLICATIONS

Wani et al., J. Am. Chem. Soc., May 1971, 93:2325–2327.
Kingston et al., J. Nat. Prod. Jul.–Aug. 1982, 45:266–470.
V. Senilh et al., J. Nat. Prod., Jan.–Feb. 1984, 47: 131–137.
Huang et al., J. Nat. Prod., Jul.–Aug. 1986, 49: 665–669.
Vidensek et al., J. Nat. Prod., Nov.–Dec. 1990, 53:1609–1610.
Blume, E., J. Natl., Cancer Inst., Aug. 1991, 83:1054–1056.
Rowinski et al., Pharmacol. Ther., 1991; 52:35–84.
Miller et al., J. Org. Chem., 1981; 46:1469.
McLaughlin et al., J. Nat. Prod., May–Jun. 1981; 44:312–319.
Fett–Neto et al., Bio/Technology, Dec. 1992; 10:1572–1575.
Kingston, Pharmacol. Ther., 1991; 52:1–34.
Kelsey et al., J. Nat. Prod., Jul. 1992; 55:912–917.
Wheeler et al., J. Nat. Prod., Apr. 1992; 55:432–440.
K. Witherup et al., "High Performances liquid chromatographic separation of taxol and related compounds from taxus brevifolia", Journal of Liquid Chromatography Dec. 1989; 12(11), pp. 2117–2132.

* cited by examiner

Primary Examiner—Ba K. Trinh
(74) Attorney, Agent, or Firm—Darby & Darby

(57) ABSTRACT

Disclosed is a process for isolating and purifying paclitaxel from a natural resource of taxanes, comprising the steps of (a) washing a raw material comprising paclitaxel with water in order to remove soluble impurities from the raw material; (b) extracting with an organic solvent a wet raw material comprising paclitaxel; (c) contacting the wet raw material with a salt to obtain a biomass by precipitation, isolation, and drying; (d) removing resin and natural pigments from the dried biomass by dissolving the biomass in acetone or an acetone-hexane mixture, and adding at least one polar solvent until a paclitaxel-enriched oil phase is obtained; and (e) chromatography purifying the paclitaxel-enriched oil phase in a volatile solvent to obtain a purified solution, followed by crystallization.

22 Claims, 6 Drawing Sheets

PROCESS FOR ISOLATION AND PURIFICATION OF PACLITAXEL FROM NATURAL SOURCES

FIELD OF THE INVENTION

The present invention relates to an improved process for the isolation and purification of Paclitaxel from natural sources.

BRIEF DESCRIPTION OF THE PRIOR ART

U.S. Pat. No. 6,452,024 and its foreign counterparts all in the name of the present Applicant, CHAICHEM PHARMACEUTICALS INTERNATIONAL, disclose and claim a process of the above mentioned type, which is particularly interesting as compared to all the previous processes disclosed as "prior art in the preamble of this U.S. patent. More specifically, the process disclosed in this U.S. patent is interesting inasmuch as it permits:

- to make easier the obtention of a biomass after extraction of the barks, needles and/or branches of Taxus of different species;
- to increase the amount of biomass which is so obtained and has to be purified by chromatography;
- to reduce the steps of purification;
- to increase the amount of obtained Paclitaxel; and
- to reduce the production cost to a more economical level.

The process disclosed in this U.S. Pat. No. 6,452,024 basically comprises the following steps:

a) extracting a raw material comprising Paclitaxel from a natural source of taxanes with an organic solvent;

b) contacting the raw material with a basic medium or an acidic medium to obtain a biomass by precipitation, isolating and drying said biomass;

c) removing resin and natural pigments from the isolated and dried biomass by dissolving the biomass in acetone and then adding to it at least one non-polar solvent such as hexane or heptane, until a Paclitaxel-enriched oily phase is obtained;

d) contacting the Paclitaxel-enriched oily phase recovered in the preceding step with an acidic medium when step (b) was carried out with a basic medium, or with a basic medium when step (b) was carried out with an acidic medium, in order to obtain a precipitate by precipitation, isolating the precipitate and drying it; and e) chromatographically purifying at least once a solution of the isolated precipitate in a volatile solvent, and crystallizing at least once the purified solution obtained by chromatography.

In the above U.S. patent, it is also disclosed that step (e) preferably comprises:

$e_1$) a first chromatographic purification comprising dissolving the precipitate isolated ion step (d) in a volatile solvent, preparing a mixture of the so-obtained solution with silica gel, treating the mixture in a chromatographic column containing silica gel, and recovering Paclitaxel-enriched fractions;

$e_2$) a second chromatographic purification comprising by evaporating to dryness the Paclitaxel-enriched fractions recovered in the preceding step until a residue is obtained, and preparing a mixture by solubilizing said residue in a volatile solvent, the mixture being repurified by chromatography under the same conditions as in the preceding sub-step in order to obtain other Paclitaxel-enriched fractions;

$e_3$) a first crystallization comprising evaporating to dryness the other Paclitaxel-enriched fractions obtained in the preceding sub-step until a residue is obtained, preparing a mixture of this residue in acetone and crystallizing the Paclitaxel contained in the mixture with a non-polar solvent;

$e_4$) a second crystallization comprising solubilizing in acetone Paclitaxel crystals obtained in the preceding sub-step and recrystallizing the Paclitaxel under the same conditions as in the preceding sub-step;

$e_5$) a third chromatography purification comprising solubilizing the crystals obtained by recrystallization in the preceding sub-step in a volatile solvent to obtain a solution, preparing a mixture of this solution with silica gel and treating said mixture in a chromatographic column containing silica gel in order to obtain, with an elution solvent, further Paclitaxel-enriched fractions; and $e_6$) a third crystallization comprising evaporating to dryness the further Paclitaxel-enriched fractions obtained in the preceding sub-step until a residue is obtained, solubilizing the residue in an alcohol, cetone or an alcohol-cetone mixture to obtain another mixture, and crystallizing the Paclitaxel contained in the other mixture with water.

As aforesaid, the process disclosed in the above U.S. Pat. No. 6,452,024 is very interesting inasmuch as it is much simpler, efficient and cost-effective than the existing processes. However, this process still calls for numerous steps of separation by chromatography and purification by crystallization that are necessary to remove the large quantities of solvent-soluble impurities that are obtained when the extraction is carried out using needles and twigs from natural sources of taxanes. This leads to a still high production cost due in particular to the low amount of Paclitaxel in the different species of Taxus. Moreover, the amount of biomass which can be purified, is very limited because of the small sizes of the chromatography columns and because of the low yield in Paclitaxel obtained after purification.

SUMMARY OF THE INVENTION

The object of the present invention is to provide an improved process which solves most of the problems mentioned hereinabove.

More particularly, the object of the invention is to provide an improved process which permits:

- to obtain a solution which contains the most of Paclitaxel and analogs after extraction of the barks, needles and/or branches of Taxus of different species;
- to reduce the impurities and the volume of the Paclitaxel and analogs extract with which the biomass is obtained by precipitation;
- to further increase the amount of biomass which has to be purified by chromatography;
- to further reduce the steps of purification;
- to further increase the amount of obtaining Paclitaxel; and finally
- to further reduce the production cost to a more economical level.

The improved process according to the invention for the extraction and purification of. Paclitaxel from a natural source of taxanes containing Paclitaxel, comprises the following basic steps:

a) washing with deionized or pure water, a raw material comprising Paclitaxel, said raw material coming from said natural source of taxanes, such a washing allowing removal of soluble impurities from said raw material;

b) extracting with an organic solvent from said washed raw material, a wet raw material comprising Paclitaxel;

c) contacting said wet raw material with a salt to obtain a biomass by precipitation, and isolating and drying said biomass;

d) removing resin and natural pigments from the so isolated and dried biomass by dissolving said biomass in acetone or an acetone-hexane mixture and then adding thereto at least one-polar solvent until a Paclitaxel-enriched oil phase is obtained;

e) purifying by chromatography at least once the Paclitaxel-enriched oily phase obtained in the preceding step in a volatile solvent to obtain a purified solution and crystallization at least once the purified solution obtained by chromatography.

The crystallized product that is so obtained is actually a mixture of Paclitaxel crystals, which, after filtration and drying of the crystals, basically consists of:

about 60% of crystals having a purity higher than 99%;

about 30% of crystals having a purity higher than 98% (<99%); and about 10% of crystals having a purity higher than 92% (<98%).

The crystals having purities less than 99% can be separated, mixed together and subjected to subsequent purification by chromatography in order to get more of the final product having a purity higher than 99%.

The present invention, its basic differences with respect to the closest prior art, its advantages and the way it can be reduced to practice will be better understood upon reading the following non-restrictive description made with reference to the accompanying drawings, and the appended examples.

DETAILED DESCRIPTION OF THE INVENTION

Figure 1A:
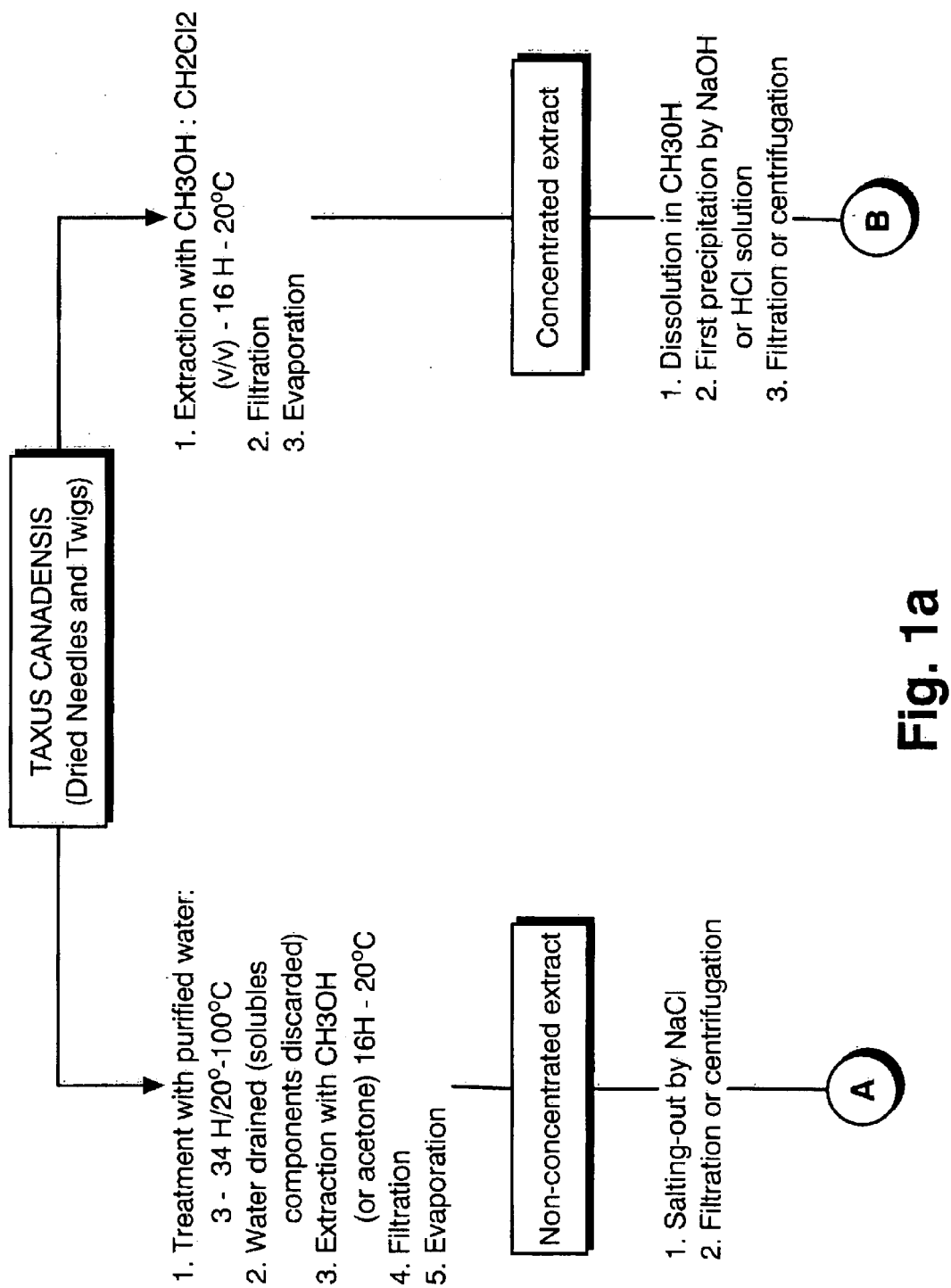
FIGS. 1a–1b, which are linked together by designated connectors, are flow charts in which the basic steps of the process according to the invention and the one disclosed in the closest prior art, namely U.S. Pat. No. 6,452,024 are compared.

As aforesaid, the improved process according to the invention is intended to be used for the extraction and purification of Paclitaxel from a raw material coming from a natural source of taxanes containing the Paclitaxel to be extracted.

The natural source of taxanes used as starting material for carrying out the process according to the invention is of Taxus gender. More particularly, it consists of any one of the species of conifers that contain Paclitaxel and its derivatives. Such species of conifer containing Paclitaxel may consist of *Taxus brevifolia, Taxus baccata, Taxus canadensis, Taxus wallichiana, Taxus yunnanensis, Taxus densiformis, Taxus hicksii, Taxus wardii, Taxus cuspidata, Taxus capitata* or *Taxus brownii*.

The process according to the invention has the advantage of being usable with any part of the natural source of taxanes which contains Paclitaxel. Preferably, use is made of barks of the selected conifer(s). Alternatively, use can be made of branches and needles of the selected conifers.

Detailed description of Each Step of the Process According to the Invention

Step 1—Washing

The first step of the improved process according to the invention consists of washing a raw material containing Paclitaxel and its analogs coming from a natural source of taxanes, using a deionized or pure water to do so. The raw material which may consist of barks, branches, needles and the like is completely covered with the water with or without stirring at a temperature comprised between 20° C. and 100° C. (preferably at a temperature of 20–25° C.) for a period of 2 to 24 hours (preferably 3 hours). After that time, water is drained. Such permits to remove water-soluble impurities from the raw material.

Step 2—Extraction

The second step of the improved process consists of extracting with an organic solvent, a wet raw material containing Paclitaxel and its analogs from the washed raw material obtained in the first step.

The organic solvent that is used during this extraction step is preferably selected from the group consisting of alcohols, cetones and mixtures thereof. As examples of such preferred solvents, reference can be made to methanol, acetone and mixtures of methanol with acetone.

In the case where one uses a mixture of an alcohol and a cetone, the alcohol and cetone are preferably present in volume ratio comprised between 9:1 and 1:9. More preferably, the volume ratio in the mixture is equal to about 1:1.

Preferably: also, the extract that is so obtained is filtered to remove deposits, and then transferred in a double wall tank in which hot water preferably at a temperature of 65–70° C., is fed. The organic solvent is distilled from this tank. Usually, the collected solvent amounts to about 70% from the starting volume. The remaining solution containing Paclitaxel is then drained into another tank. This remaining solution is actually a non-concentrated extract because of the residual water contained therein.

Step 3—Biomass Isolation

The third step of the improved process according to the invention consists of isolating a biomass from the solution obtained in the previous step.

For this purpose, the non-concentrated extract obtained from the previous step is diluted in methanol and water and then salted-out to obtain precipitation of a biomass. Sodium chloride is preferably used as salt for salting-out the extract. However, other salts could be used for the same reaction, like ammonium chloride, ammonium sulfate, sodium or potassium acetate, potassium chloride, sodium or potassium phosphate or sodium or potassium citrate, all of these salts being solubilizable in an aqueous solution.

Sodium chloride (or any other selected salt), is preferably quickly added to the non-concentrated extract under heavy stirring. The requested biomass is formed, rapidly by addition of sodium chloride in a concentration comprised between 10 and 200 grams per liter of solution. Preferably, sodium chloride is added at a concentration comprised between 50 and 100, and more preferably between 50 and 75 grams per liter of the non-concentrated extract solution.

The biomass that is formed and has precipitated, is separated from the solution by filtration or by centrifugation. The so separated biomass which is wet, can be submitted immediately to the next step or dried at ambient air or under vacuum, preferably by ventilation or lyophilization.

Step 4—Removal of Resin and Natural Pigments

The fourth step of the improved process according to the invention consists of treating the biomass isolated in the preceding step in order to remove resin and natural pigments contained therein.

The way this step may be carried out depends on the kind of biomass obtained in the previous step, namely on whether it is dried or wet.

A—When the biomass obtained from the preceding step of precipitation is dried, then it is put back in solution by adding thereto a volume of a mixture of acetone and hexane (preferably in a volume ratio of 1/1) that is preferably equal to about 1/25 of volume of the non-concentrated extract obtained in step 2, before precipitation.

More preferably, the dried biomass is put back in solution by first adding the mixture of acetone and hexane and then adding 1.5 additional volumes of pure hexane. The final ratio of acetone to hexane is 1 volume of acetone for 4 volumes of hexane. After such a dissolution the pure water is added to the obtained solution to form a Paclitaxel-enriched oily phase. Water is preferably added at a ratio of 2 to 10 volumes, and more preferably 5 to 7 volumes, per 100 volumes of added acetone.

The mixture that is so obtained is then transferred into a decanting flask. An oily phase containing Paclitaxel and other taxanes that is deposited at the bottom of the flask is recovered. This oily phase is then evaporated and ready to be purified by chromatography on silica gel.

B—When the biomass obtained just after centrifugation in the third step is wet (viz. it has not been subjected to drying), then such a wet biomass is put back in solution in an acetone and hexane mixture. (preferably in a volume ratio of 1.1) without adding any water. The volume of acetone is preferably equal to about 1/20 of the volume of the non-concentrated extract obtained in second step before precipitation.

After such a dissolution, at least one non-polar solvent is added to the obtained solution to form a Paclitaxel-enriched oily phase which is separated from hexane in the same way.

The non-polar solvent(s) used in this purpose is (are) preferably selected from the group consisting of hydrocarbons miscible with acetone, such as pentane, hexane or heptane. When use is made of hexane, the volume of hexane that is used is usually 3 to 4 times the one of the acetone solution.

In the case where the wet biomass contains too much water, the obtained Paclitaxel-enriched oily phase must be treated to remove residual water before coating it on silica gel and subjecting the so coated silica el to chromatography in order to recover and purify Paclitaxel and its analogs. Removal of water permits to dry more quickly the coated silica gel before loading it onto the chromatography column.

The residual water in the Paclitaxel-enriched oily phase can be removed by extraction with a water-immiscible solvent. The mixture is then decanted and the organic phase is separated from the water. The water-immiscible solvent that is used is preferably selected from the group consisting of halogenated hydrocarbons or ether. As examples of such solvents, reference can be made to chloromethylene, trichloromethane and to diethyl ether.

The obtained extract is the recovered, concentrated under vacuum and, at this point, ready to be purified by chromatography on silica gel.

Step 5—Chromatographic Purification

The fifth and last step of the process according to the invention consists in chromatographically purifying at least once a solution of the Paclitaxel-enriched oily phase obtained in the preceding step, and crystallizing at least once the purified solution obtained by chromatography.

To do so, the concentrated Paclitaxel-enriched oily phase obtained in the fourth step is submitted to at least one chromatographic purification and to the purified solution obtained by chromatography at least one crystallization. Preferably however, the concentrated Paclitaxel-enriched oily phase obtained in the fourth step is submitted to several chromatographic purifications and several crystallizations, the number of chromatographic purifications being preferably equal to two and the number of crystallization being preferably equal to three.

These successive purifications and crystallizations will now be described as sub-steps A to E.

A—First Chromatographic Purification

In the first chromatographic purification step, the Paclitaxel-enriched oily phase obtained in the fourth step of the process is mixed with silica gel and dried under ventilation. The silica gel coated with the oily phase is loaded onto a chromatographic column containing the same type of gel. In this column, the Paclitaxel is purified with an elution mixture comprising from 30 to 40% of acetone and from 60 to 70% of hexane. Preferably, the elution mixture comprises about 35% of acetone and about 65% of hexane.

The column that is used preferably has a height of 142 cm and inside diameter of 7.6 cm or 15.2 cm depending of the amount of Paclitaxel to be purified. A Paclitaxel-enriched oily phase containing 4 to 6 g of Paclitaxel is preferably purified in a column having a 7.6 cm diameter. An oily phase containing 20 to 24 g of Paclitaxel uses a column having a 15.2 cm column diameter. The smaller column (7.6 cm diameter) contains 2,2 to 2.3 kg of silica gel while the bigger column (15.2 cm diameter) contains 8 to 9 kg.

The silica gel of the column is washed and balanced with the elution mixture consisting of acetone and hexane. Elution of the fraction is carried out with the same solvent mixture preferably at a flow rate of about 100 ml/min in the 7.6 cm diameter column, and a flow rate of 400 ml/min in the 15.2 cm diameter column. In both cases, the volume is preferably kept under a pressure varying from 0 to 30 psi.

B—First Crystallization

B.1—In this step, the fractions containing Paclitaxel obtained by chromatography in the preceding step, are evaporated to dryness and put back in solution in acetone. The amount of acetone is adjusted to obtain an absorbency at 228 nm of 1.0 to 1.5 O.D. for the maximum of the peak corresponding to Paclitaxel by HPLC analysis. Then, the Paclitaxel is crystallized by adding from 3 to 4 volumes of hexane in the acetone solution.

B.2—Alternatively, the fractions containing Paclitaxel obtained by chromatography in the preceding step, are reduced by evaporating to 1/5 of initial volume or until obtention of 1.0 to 1.5 O.D. for the maximum of the peak corresponding to Paclitaxel by HPLC analysis. The Paclitaxel thus remains in the solvent mixture of acetone-hexane (35–65%). Then, the Paclitaxel is crystallized by adding from 2 to 3 volumes of hexane in the solution.

Crystals are formed rapidly. The mixture is left overnight at ambient temperature or at a temperature between 2 and 8° C. to complete crystallization.

C—Second Crystallization

In this step, the crystals obtained by crystallization in the preceding step are separated by filtration or centrifugation and put back in solution in acetone with a volume of acetone adjusted to obtain an absorbency of the solution varying from 1.0 to 1.5 O.D. for the peak corresponding to Paclitaxel by HPLC analysis.

The Paclitaxel contained in this solution is then recrystallized by adding to the acetone solution from 3 to 4 volumes of hexane per volume of solution.

The crystals obtained in this step have a Paclitaxel purity comprised between 85–95% by HPLC analysis.

After crystals separation by filtration from the two previous crystallisation steps, the hexane phase is mixed with the fractions obtained from the first chromatography corresponding to the peak which is identified as 9-dihydro 13-acetylbaccatin III. This component is eluted in several fractions before reaching the Paclitaxel peak. The mixture is then evaporated to dryness. The so obtained residue is converted into light yellow crystals of 9-dihydro-13-acetylbaccatin III by addition of methanol. The crystals are separated by filtration, then put back in solution in acetone and crystallized rapidly by adding 4 volumes of hexane. The crystals of 9-dihydro-13-acetylbaccatin III obtained in this step by filtration can be recrystallized by the same method as disclosed above and have a purity higher than 98% by HPLC analysis.

D—Second Chromatographic Purification

D.1 In this step, the Paclitaxel crystals obtained in the preceding step are filtered and then put back in solution in acetone. The Paclitaxel solution is filtered to remove particles undissolved in the acetone. The so obtained solution is then mixed with silica gel and dried under ventilation.

The silica gel coated with Paclitaxel is loaded onto a chromatographic column containing the same type of gel. Paclitaxel is then repurified for a second time with an organic-solvent based elution mixture. Preferably, the elution mixture comprises from 30 to 40% acetone and from 70 to 60% hexane.

More preferably, the crystals obtained in step C are dissolved with acetone, mixed with silica gel and dried. The gel impregnated with Paclitaxel is loaded onto a chromatographic column (preferably 142 cm long with a 7.6 cm or 15.2 cm inside diameter, depending on the amount of Paclitaxel to be purified). The 7.6 cm diameter column may contain 2,2 to 2.3 kg of silica gel while the 15.2 cm diameter column may contain 8 kg of silica gel. The gel in the column is washed and equilibrated with a solvent consisting of acetone and hexane (preferably 35:65% per volume). Elution of the fractions is carried out with the same mixture of solvents, preferably at a flow rate of about 100 ml/min within the 7.6 cm diameter column or 400 ml/min within the 15.2 cm diameter column. Both columns are operated at a pressure varying from 0 to 30 psi.

D.2 Alternatively, the Paclitaxel crystals obtained in the preceding step C are filtered and then put back in solution in methylene chloride. The Paclitaxel solution is filtered to remove particles undissolved in the chloride methylene.

The so obtained solution is then mixed with silica gel and dried under ventilation.

The silica gel coated with Paclitaxel is loaded onto a chromatographic column containing the same type of gel. Paclitaxel is then repurified for the second time with an organic-solvent based elution mixture. Preferably, the elution mixture comprises from 95 to 98% chloromethylene and from 2 to 5% isopropanol.

More preferably, the crystals obtained in step C are dissolved with chloromethylene, mixed with silica gel and dried. The gel impregnated with Paclitaxel is loaded onto a chromatographic column (preferably 142 cm long with a 7.6 cm or 15.2 cm inside diameter, depending on the amount of Paclitaxel to be purified). The 7.6 cm diameter column may contain 2.2 to 2.3 kg of silica gel while the 15.2 cm diameter column may contain 8 kg of silica gel. The gel in the column is washed and equilibrated with a solvent consisting of chloromethylene and isopropanol (preferably 97.5:2.5% per volume). Elution of the fractions is carried out with the same mixture of solvents, preferably at a flow rate of about 100 ml/min with the 7.6 cm diameter column or 400 ml/min with the 15.2 cm. diameter column.

E—Third Crystallization

In this step, the enriched fractions containing Paclitaxel recovered by chromatography in step D are combined according to their purity, preferably according to purities of 98 to 99% and 90 to 98%. Then, they are evaporated to dryness and put back in solution in acetone, alcohol (ethanol) ethyl acetate or diethyl ether.

The volume of added acetone is adjusted to obtain an absorbency varying from 1.0 to 1.5 O.D. for the peak corresponding to Paclitaxel according to HPLC analysis. When use is made of the other solvents mentioned above, namely alcohol (ethanol), ethyl acetate or diethyl ether, the Paclitaxel concentration is much more important, in general 5 times more than concentrated than Paclitaxel in acetone solution.

The Paclitaxel is then recrystallized for a third time, preferably as follows:

1. by adding to the acetone solution 3 to 4 volumes of hexane per volume of acetone.
2. by adding to the alcohol solution or ethyl acetate solution at least 3 volumes of hexane per volume of alcohol or ethyl acetate.
3. by adding to the diethyl ether solution at least 2 volumes of hexane per volume of diethyl ether.

In the last step of purification and recrystallization disclosed hereinabove, addition of hexane in the Paclitaxel solution can be carried out at ambient temperature. This will slow down the formation of crystals but crystallization will be completed overnight at 2–4° C. or at ambient temperature. The crystals are filtered and dried under vacuum, in order to obtain a fine, detached powder. The crystals are then dissolved in alcohol (methanol or ethanol) or in acetone and then put back in suspension in water and lyophilized during 66 to 72 hours at a temperature of about −60° C.

The obtained fractions of taxanes can then be analyzed by HPLC chromatography (Waters system) using an Autosampler (Waters 717 plus), a Photodiode Array Detector (Waters 996), a Multisolvent Delivery System (Waters 600E) and a C18 Nova-Pak column, 60 Å, 4 $\mu$m (3.9×150 mm).

Analysis of the fractions can be carried out by injecting a volume of 5 $\mu$l. The column is eluted at a flow rate of 1ml/min using a solvent gradient of acetonitrile-water-methanol (25:50:30 in volume at the beginning and 35:35:30 at the end).

The peaks of the compounds are detected at 228 nm and the time of analysis of a sample is about 36 minutes. The retention time for the Paclitaxel peak is about 18.9±0.2 minutes and 6.5±0.2 minutes for the 9-dihydro13-acetylbaccatin III peak.

Preferably, the volatile solvent used in the chromatographic purification step for the solubilization of the residue is selected from the group consisting of cetones, C1–C3 light alcohols, ethyl acetate, chloromethylene or a mixture of these solvents.

At the end of this step E, after crystallization of the Paclitaxel in hexane and after filtering and drying, a mixture of Paclitaxel crystals is obtained. This mixture of Paclitaxel crystals consists of:

60% of crystals having a purity higher than 99%,

30% of crystals having a purity higher than 98% but lower than 99%, and

10% of crystals having a purity higher than 92% but lower than 98%.

Basic Differences Between the Present Invention and the One Disclosed and Claimed in Applicant's U.S. Pat. No. 6,452,024

Figure 1B:
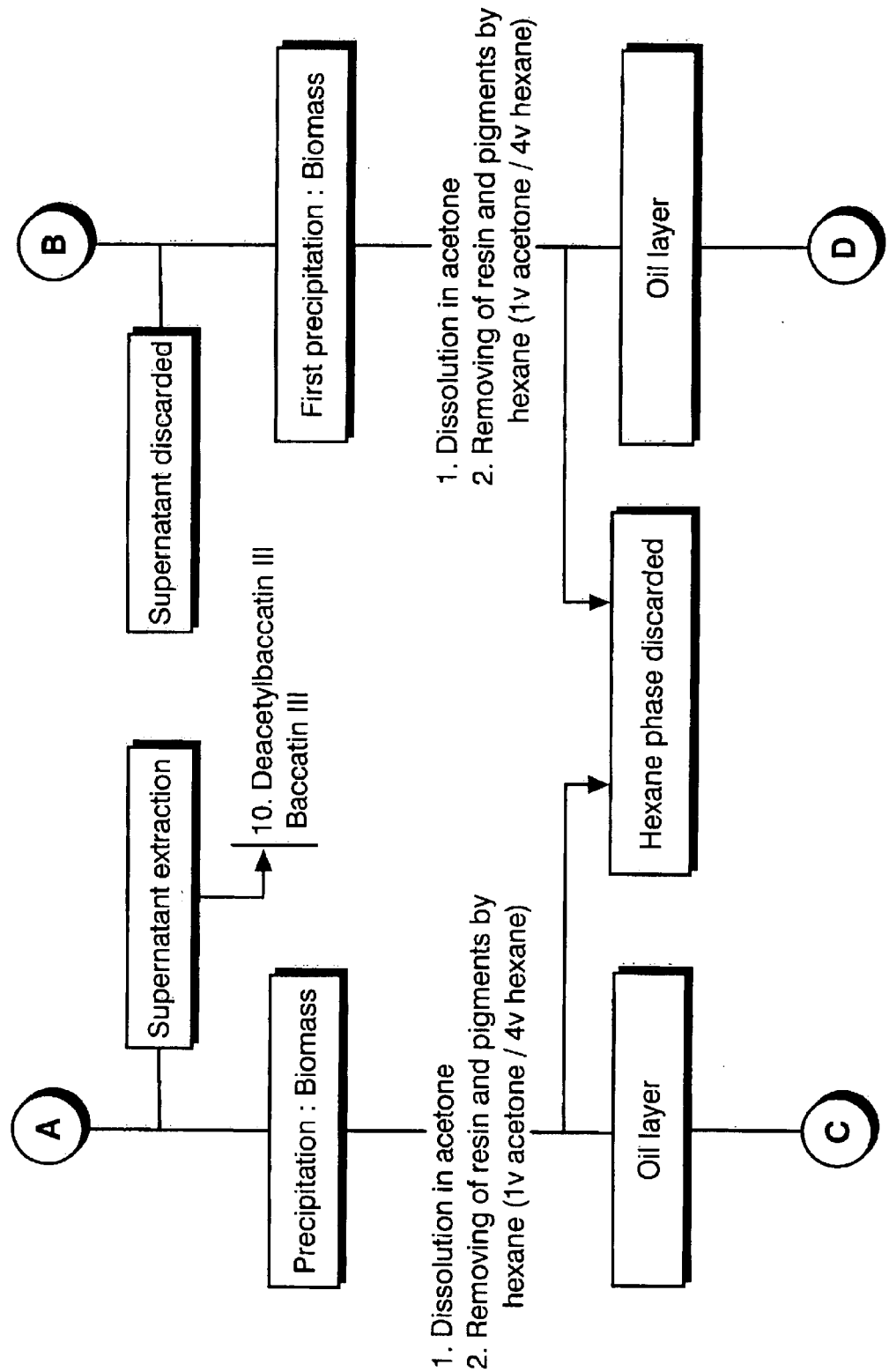
Figure 1C:
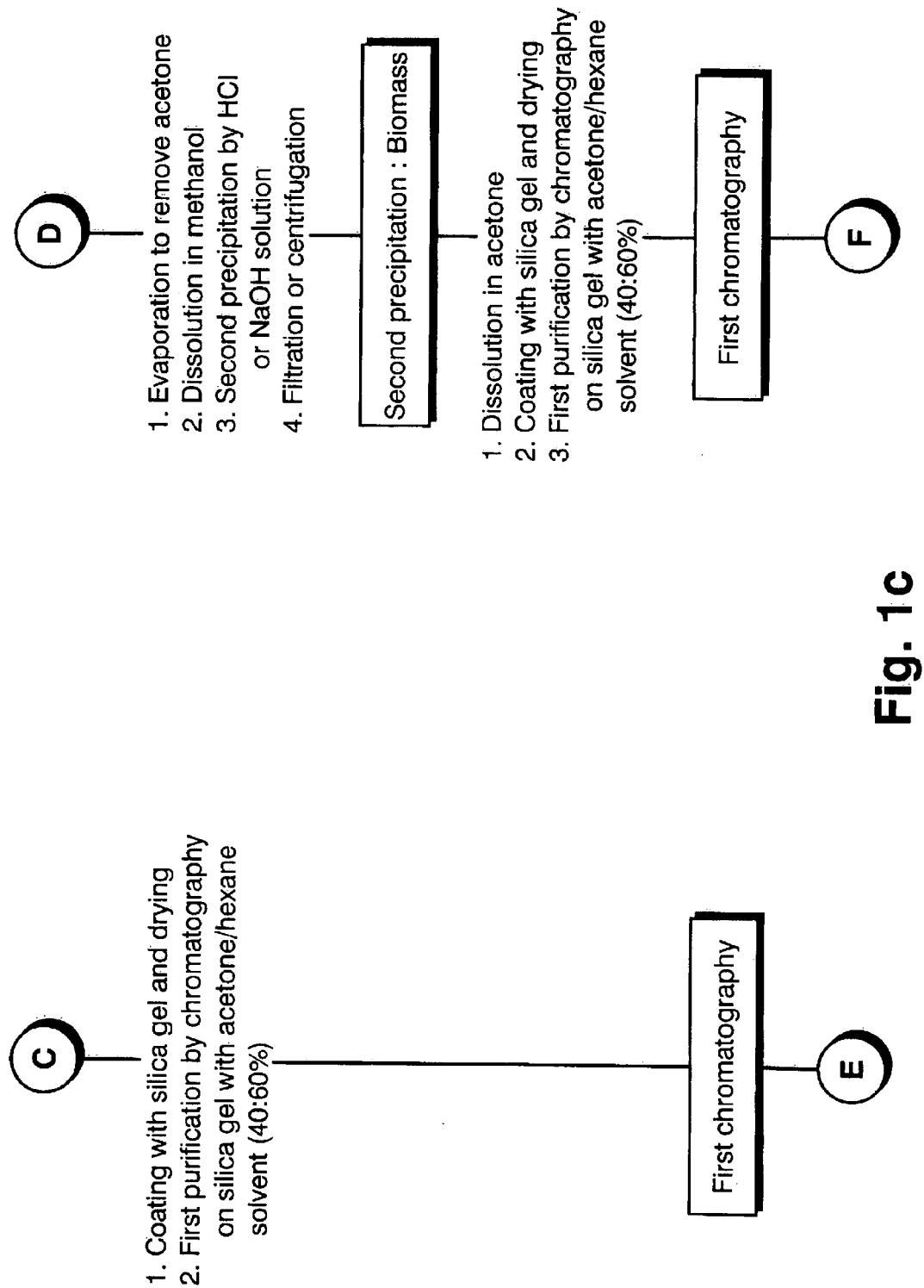
Figure 1D:
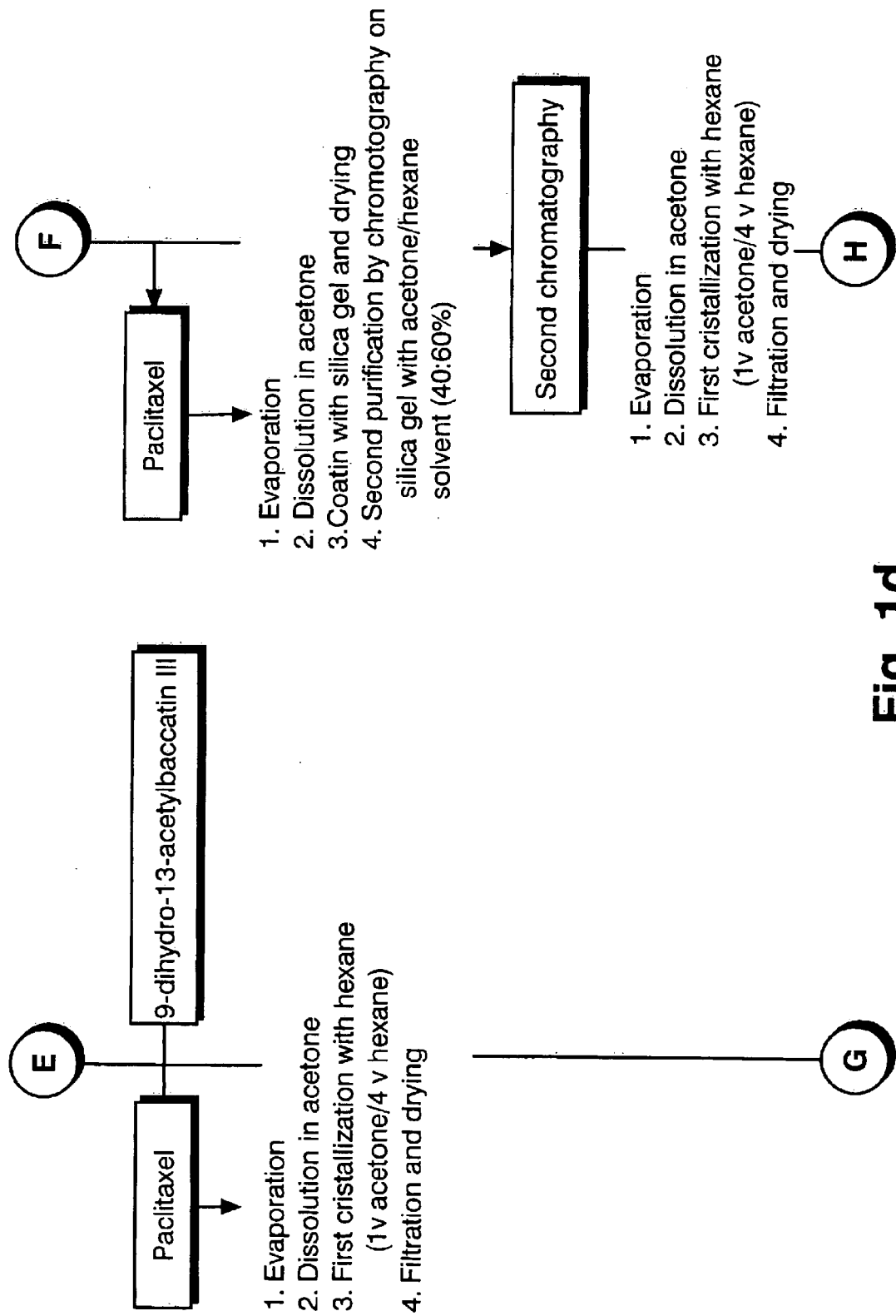
Figure 1E:
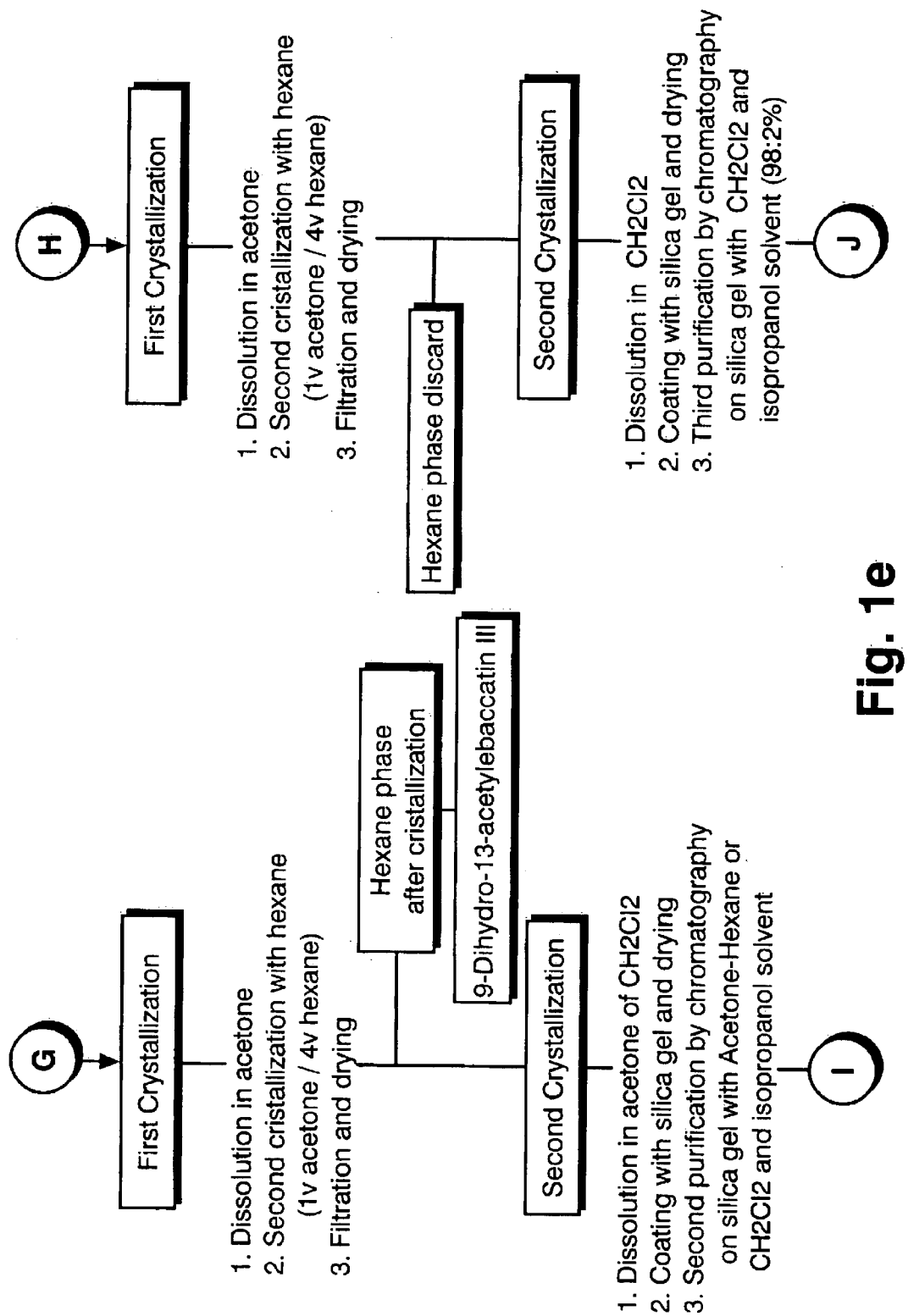
Figure 1F:
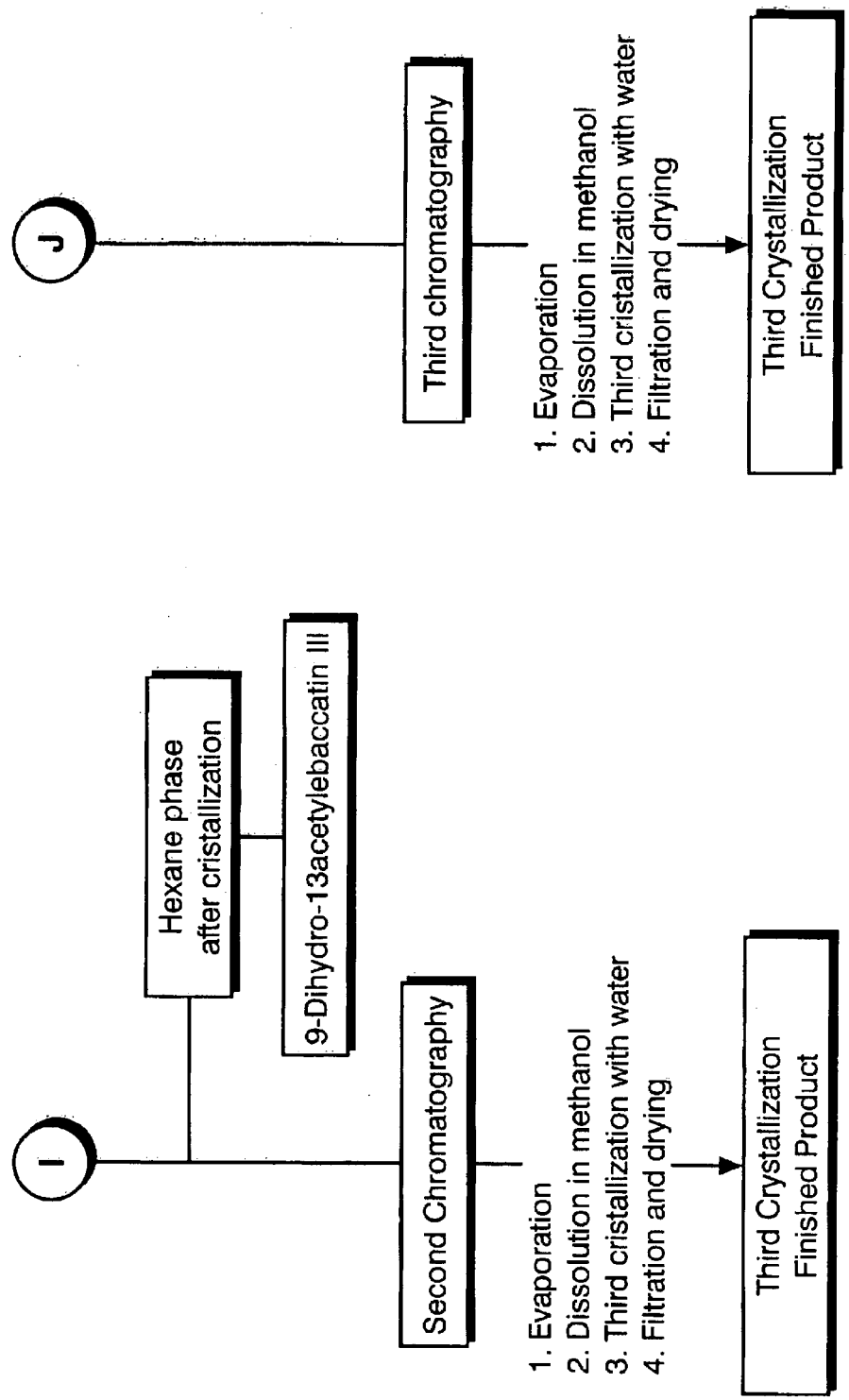

As aforesaid, FIGS. 1a–1b are flow charts in which the basic steps of process disclosed and claimed in U.S. Pat. No. 6,452,024 are compared with those of the present invention:

1. As is shown in these flow charts, in the process according to the invention, the raw material containing the Paclitaxel to be extracted, which preferably consists of dried needles and twigs, is washed in purified water before extraction by organic solvent such as methanol or acetone. The water obtained after such a washing contains some hydrosoluble components which are discarded. The wet needles and twigs are then "covered" with methanol or acetone, or a mixture of both, and subjected to extraction for a period of, for example, 16 hours at 20° C. The extract is then passed through a cartridge filter and pumped into a double wall tank where the solvent is distilled by circulation of heated water in the jacket. As aforesaid, the extract containing some residual water is called "non-concentrated extract".

In contrast, in U.S. Pat. No. 6,452,024, the extraction of the dried needles and twigs is done directly, using a solvent mixture of methanol and methylene chloride. The obtained concentrated extract after distillation is very visquous and contains an important amount of resin and natural pigments. This extract can be called "concentrated extract".

2. In the process according to the invention, sodium chloride is added to the non-concentrated extract to form a biomass that is precipitated immediately. This biomass is isolated by centrifugation.

In U.S. Pat. No. 6,452,024, the biomass is obtained by precipitation of the concentrated extract previously diluted in methanol in a basic or acidic medium. The precipitate that is formed is very fine and light and is salted out before isolation by addition of sodium chloride.

3. Then, in the process according to the invention as well as in the one disclosed in U.S. Pat. No. 6,452,024, the biomass is dissolved in acetone and a given amount (preferably 4 volumes) of a non-polar solvent such as hexane, is added to the acetone solution to form a Paclitaxel-enriched oily phase.

However, in the process according to the invention, the so obtained, Paclitaxel-enriched oily phase is ready to be purified in a chromatographic column with silica-gel at low pressure. In contrast, in the process disclosed in U.S. Pat. No. 6,452,024, the obtained Paclitaxel-enriched oily phase must be submitted to a second precipitation in acidic or basic medium. The precipitate is isolated by centrifugation after having been salted-out by addition of sodium chloride. The obtained precipitate is dried and then dissolved in acetone. It is only at that time that the acetone solution is ready to be purified in a chromatographic column with silica-gel at low pressure.

4. In the first chromatographic purification step of the process according to the invention, the Paclitaxel-enriched oily phase is mixed with silica gel and dried under ventilation. Then the silica gel covered with the biomass is loaded onto a chromatographic column. The Paclitaxel is purified with an elution mixture of acetone and hexane. The fractions containing Paclitaxel obtained by chromatography are grouped together and then crystallized. The crystals obtained by filtration or centrifugation are dissolved in acetone and then recrystallized for a second time. The crystals are isolated by filtration or centrifugation and ready to be repurified by a second and last chromatographic column with silica gel at low pressure.

In the first chromatographic purification step of the process disclosed in U.S. Pat. No. 6,452,024, the Paclitaxel-enriched oily phase is mixed with silica gel and dried under ventilation. Then the silica gel covered with the biomass is loaded onto a chromatographic column. The Paclitaxel is purified with an elution mixture of acetone and hexane. The fractions containing Paclitaxel obtained by chromatography are grouped together and then repurified by a second chromatographic column in the conditions used for the preceding step. The fractions containing the Paclitaxel obtained by the second chromatography are grouped together and then crystallized. The crystals obtained by filtration or centrifugation are dissolved in acetone and then recrystallized for a second time. The crystals are isolated by filtration or centrifugation and ready to be repurified by third and last chromatographic column with silica-gel at low pressure.

Thus, in the process disclosed in U.S. Pat. No. 6,452,024, the number of chromatographies to be carried out is higher (3 instead of 2).

5. In both cases of course, the fractions containing Paclitaxel from the second and last chromatographic column in this invention or those from the third and the last chromatographic column in U.S. Pat. No. 6,452,024 are grouped together and then crystallized to form a final product.

Thus, as it can now be better understood, a main advantage of the present invention as compared with the one of U.S. Pat. No. 6,452,024 are that the process according to the invention comprises less preparation steps from the one of starting extraction of the needles to the obtention of the biomass, and less purification steps: two chromatographies in place of three as described in U.S. Pat. No. 6,452,024.

The process according to the invention also uses much less solvents and needs much less raw materials for obtaining the same amount of final product. Therefore, the production cost with the improved process according to the present invention is much lower than not only the usual and traditional processes used for Paclitaxel purification but also the one of U.S. Pat. No. 6,452,024.

EXAMPLES

The following examples are given for the sole purpose of illustration and should not be considered as to limit the scope of the present invention.

Example 1

Washing 100 kg of dried and ground needles and twigs of Taxus canadensis were placed into a cotton bag. This bag was put into a stainless steel tank in which 400 L of distilled water were added. The cotton bag was completely immersed under water for a period of 3 hours at room temperature and the solution containing water-soluble impurities was drained.

In practice, this washing procedure may be repeated once or twice, the wet needles being kept in the tank by the cotton bag.

Extraction

250 L of methanol were added into the tank containing the wet needles and twigs. Extraction was carried out during 16 hours at ambient temperature. The extract was pumped though filters into a second double wall tank. The methanol was distilled with the aid of hot water at 80° C. circulating in the double wall of the tank. The recovered methanol was transferred into the tank containing needles for rinsing and the volume of pure methanol was completed to 400 L. The rinsed methanol was then pumped and distilled until about 75% of the methanol volume was recuperated. The residual solution of about 100 to 120 L, hereinafter called "non-concentrated extract", was transferred into another tank and was kept until the temperature of the extract decreased to ambient temperature.

Precipitation of Biomass by Salting-out

The non-concentrated extract was clarified with 10 L of methanol (about 10% of methanol as compared to the volume of non-concentrated extract volume). The biomass was isolated by precipitation by adding rapidly sodium chloride under stirring. The concentration of sodium chloride was about 50 g per liter of the extract solution. A precipitate was formed immediately and the mixture was kept without stirring overnight. The supernatant was then drained and the heavy precipitate was easily recovered without filtration or centrifugation.

If needs be, the biomass obtained by adding sodium chloride may be recovered rapidly by filtration or centrifugation at a speed of 4,200 rpm at 20° C. during 30 minutes (J6 MC Beckman Centrifugal machine, 4.2 JS rotor). It is understood that a continuous flow centrifugal machine may preferably be used to process large amount of precipitate.

A supernatant containing 10-deacetylbaccatin III and Baccatin III was extracted by methylene chloride or diethylether. The organic phase was concentrated by evaporation and may be treated to extract these analogs of taxane.

Removal of Resin and Pigments

1. The obtained precipitate was air dried. Alternatively, it could have been vacuum dried or lyophilized (Freeze dryer—FTS System). The weight of the precipitate was about 1.3 kg–1.5 kg. This precipitate was solubilized in 6L of an acetone-hexane; mixture (1:1) and filtered (or alternatively centrifuged at 4,200 rpm) at 0–2° C. during 30 minutes, in order to remove the insoluble particles contained therein. Then, the acetone-hexane solution was transferred into a beaker and mixed with 1.5 volumes of pure hexane (9L) by successive addition of 1/2 volume of hexane each under agitation for few minutes, the oily phase was formed by addition of between 5% and 20% of pure water, preferably 5% to 10%. The amount of water was calculated according to the volume of the acetone used. The mixture was then fed into a separating flask and allowed to partition for about 30 minutes. The Paclitaxel-enriched phase was recovered at the bottom of the flask and concentrated by evaporation to 1/10 of the initial volume of the solution obtained before percolorization. This preparation was ready to be adsorbed on silica gel for a chromatography purification step.

2. After centrifugation without drying, the so obtained precipitate was dissolved in 3 L of acetone and filtered (or, alternatively centrifuged at 4,200 rpm) at 0–2° C. during 30 minutes, in order to remove the insoluble particles contained therein. Then, the acetone solution was transferred into a beaker and mixed with 4 volumes of hexane (12 L) by successive addition of one volume of hexane each under agitation for a few minutes. The oily phase was formed quickly. The mixture was then fed into a separating flask and allowed to partition for about 30 minutes. The Paclitaxel-enriched phase was recovered at the bottom of the flask. This solution contained some residual water and thus was extracted by adding 1 volume of chloromethylene.

The water was partitioned from this mixture and the lower chloromethylene phase containing the Paclitaxel was concentrated to 1/5 of the initial volume of the acetone solution obtained before removal of the resin and pigments or evaporated to dryness. In the latter case, the dried residue was dissolved in 0.5 L of acetone.

Example 2

First Purification by Chromatography on Silica Gel at Low Pressure

The obtained acetone solution containing Paclitaxel and analogs after removal of the resin and pigments in example 1 was mixed with 500 g of silica gel (230–400 mesh). The gel impregnated with the extract was air dried under ventilation (or under vacuum). The total weight after drying was about 900–950 g and half of this material was loaded onto a column (142×7.6 cm inside diameter) containing 2.2 kg of silica gel (230–400 mesh). The gel was washed and balanced with a mixture of acetone and hexane (35:65%, volume per volume). Elution was carried out with the same solvent, using a Dynamax® solvent delivery system. The flow rate of the elution was about 100 ml/min under a pressure between 0–30 psi. The volume of solvent mixture was about 40 L and each fraction was collected in batches of 1 L. HPLC analysis indicated that there were 9 to 10 fractions, from the $26^{th}$ or $27^{th}$ to $35^{th}$ or $36^{th}$, which contained about 0.2 mg/ml to 0.7 mg/ml of Paclitaxel and their purity varied from 10 to 58%. The fractions that contained more Paclitaxel have higher purity. The quantity of Paclitaxel for each fraction was determined from its peak area by comparison with the area of a Paclitaxel standard.

It is worth noting that the fractions containing Paclitaxel can be offset with respect to the others from one purification to the other.

The fractions with the highest quantities of contaminants were discarded. In general, the first fractions which contained less than 0.3 mg/ml of Paclitaxel, were eliminated.

Example 3

First Purification by Chromatography on Silica Gel at Low Pressure

The obtained acetone solution containing Paclitaxel and analogs after removal of resin and pigments in example 1 was mixed with 500 g of silica gel (230–400 mesh). The gel impregnated with the extract was air dried under ventilation (or under vacuum). The total weight after drying was about 920 g and half of this material was loaded onto a column (142×7.6 cm inside diameter) containing 2.2 kg of silica gel (230–400 mesh). The gel was washed and balanced with a mixture of acetone and hexane (40:60%, volume per volume). The elution was carried out with the same solvent, using a Dynamax® solvent delivery system. The flow rate of the elution was about 100 ml/min under a pressure between 0–30 psi. The volume of solvent mixture was about 30 L and each fraction was collected in batches of 1 L. HPLC analysis indicated that there were 7 to 8 fractions, from the $16^{th}$ or $17_{th}$ to $23^{th}$ or $24_{th}$, which contained about 0.1 mg/ml to 0.7 mg/ml of Paclitaxel and their purity varied from 8 to 45%. The fractions that contained more Paclitaxel have higher purity. The quantity of Paclitaxel for each fraction was determined from its peak area by comparison with the area of a Paclitaxel standard.

Once again, it is worth noting that the fractions containing Paclitaxel can be offset with respect to the others from one purification to the other.

The fractions with the highest quantities of contaminants were discarded. In general, the first fractions which contained less than 0.3 mg/ml of Paclitaxel, were eliminated.

Example 4

First Crystallization

After the first chromatography purification in examples 2 and 3, the fractions with a concentration of Paclitaxel higher than 0.3 mg/ml were combined and evaporated to dryness. The residue was dissolved in acetone and the volume of acetone was adjusted to obtain a maximum peak of Paclitaxel in the 1.0 to 1.5 O.D range by HPLC. 4 volumes of hexane were then added to the acetone solution to start the crystallization during the following hour. The mixture was kept at 2–8° C. or at room temperature overnight to complete the crystallization.

Second Crystallization

Then, the obtained crystals were filtered (or centrifuged) and dissolved in acetone. The volume of acetone was adjusted to obtain a Paclitaxel peak by HPLC with a maximum O.D. in the range of 1.0 to 1.5. Hexane was then added at a ratio of 4 volumes by respect to the acetone solution. Crystals were formed in the following hour. The mixture was kept at a temperature comprised between 2–8° C. or at ambient temperature overnight to complete the crystallization. The crystals were filtered or centrifuged and dried under air or vacuum. HPLC analysis indicated that the Paclitaxel content was about 85% or higher.

Direct Isolation and First Crystallization of 9-Dihydro-13-acetylbaccatin III

The fractions containing 9-dihydro-13-acetylbaccatin III (fraction $20^{th}$ to $25^{th}$) obtained from the first purification by chromatography in example 2 or fraction $13^{th}$ to $15_{th}$ in example 3 were combined together with the hexane/acetone solutions (mother liquors) obtained from the first and second crystallization steps, containing 9-Dihydro-13-acetylbaccatin III and evaporated to dryness. The crystals were formed by adding methanol and recuperated by filtration or centrifugation. The obtained crystals were dissolved in acetone and crystallized by 3 volumes of hexane. The product was identified as 9-dihydro-13-acetylbaccatin III with a purity >95%.

Second crystallization of 9-Dihydro-13-acetylbaccatin III

The so obtained 9-dihydro-13-acetylbaccatin III crystals were dissolved in acetone and then 1 volume of hexane was added into the acetone solution. The mixture was agitated slowly and a 2 volumes of hexane additional were added. The solution was allowed to crystallize slowly. The white crystals were recovered by filtration or centrifugation and dried under ventilation or vaccum. HPLC analysis of these crystals indicated that the 9-dihydro-13-acetylbaccatin III content was equal or better than 98%.

Example 5

Second Purification by Chromatography on Silica Gel at Low Pressure

The Paclitaxel crystals obtained after the second crystallization in example 4 were dissolved in 75 to 100 ml of acetone, then filtered to remove insoluble particles and adsorbed on 75 to 100 g of silica gel. The gel coated with Paclitaxel was air dried under ventilation or under vacuum. The dried gel was loaded on top of a column (142×7.6 cm inside diameter) containing 2.2 kg of silica gel (230–400 mesh). The gel was washed and balanced with a mixture of acetone and hexane (35:65 volume per volume). The elution was carried out with the same solvent, using a Dynamax® solvent delivery system at a flow rate of about 100 ml/min under a pressure between 0–30 psi. The volume of solvent mixture was about 40 L and fractions were collected in batches of 1 L. HPLC analysis indicated that there were 9 to 10 fractions, from the $26^{th}$ or $27^{th}$ to $34^{th}$ or $35^{th}$, which contained about 0.2 mg/ml to 0.6 mg/ml of Paclitaxel and their purity varied from 85% to 99%. The fractions containing Paclitaxel having a purity higher than 98% were combined together for a third and last crystallization.

Once again, the fractions containing Paclitaxel can be offset with respect to the others from one purification step to the other.

Example 6

Second Purification by Chromatography on Silica gel at Low Pressure

The Paclitaxel crystals obtained after the second crystallization in the example 4 were dissolved in 75 to 100 ml of methylene chloride, then filtered to remove insoluble particles and then put into contact with 75 g to 100 g of silica gel. The gel coated with Paclitaxel was air dried under ventilation or under vacuum. The dried gel was loaded on top of a column (142–7.6 cm inside diameter) containing 2.2 kg of silica gel (230–400 mesh). The gel was washed and balanced with a mixture of chloromethylene and isopropanol (97.5:2.5 volume per volume). The elution was carried out with the same solvent, using a Dynamax solvent delivery system at a flow rate of about 100 ml/min under a pressure between 0–30 psi. The volume of solvent mixture was about 50 L and fractions were collected in batches of 1 L. HPLC analysis indicated that there were 20 fractions, from the $28^{th}$ to $48^{th}$, which contained about 0.1 mg/ml to 0.3 mg/ml of Paclitaxel and their purity varied from 98 to >99%. The fractions containing Paclitaxel having a purity higher than 98% were combined together for a third and last crystallization.

Third Crystallization

After the second chromatography purification of example 5 or example 6, the fractions with a purity of Paclitaxel higher than 98% were combined and evaporated to dryness. The residue was dissolved in acetone and the volume of acetone was adjusted to obtain a maximum peak of Paclitaxel in the 1.0 to 1.5 O.D range by HPLC. 4 volumes of hexane were then added to the acetone solution to start the crystallization during the following hour. The mixture was kept at 2–8° C. or at room temperature overnight to complete the crystallization.

The white crystals were recovered by filtration or centrifugation and dried under ventilation or vaccum. The purities of the crystals analysed by HPLC were as follows:

99.20 to 99.50% when obtained by example 5; and 99.50 to 99.90% when obtained in example 6.

As disclosed hereinabove, the residues obtained from the fractions containing Paclitaxel after the second chromatographic purification may be dissolved in ethanol, ethyl acetate or diethyl ether. The volume of those solvents is 5 times less than acetone used previously, its means the Paclitaxel concentration is 5 times higher (about 10 mg/ml).

In practice:

1 to 2 volumes of hexane was then added to the ether solution; and, alternatively 3 to 4 volumes of hexane was then added to the ethanol or ethyl acetate solution to start the crystallization during the following hour.

The mixture was kept at 2–8° C. or at room temperature overnight to complete the crystallization. The purities of those crystals were very similar while using acetone for crystallization.

The crystals which had a purity inferior to 98% were kept and repurified together by chromatography in the same conditions as in the second purification described: above. This repurification allows to still obtain around 75% of the total quantity of these crystals with a purity superior to 99%.

The crystals were dissolved in a minimum volume of ethanol or methanol or acetone and then put back in the vial containing the pure water. The volume of solvent was about 10 to 15% in relation to the volume of pure water. The Paclitaxel was lyophilized during 72 hours and the temperature was ramped from −60° C. to +20° C. at 0.02° C. per minute and under a pressure at 100 millitorrs.

What is claimed is:

1. Process for extraction and purification of Paclitaxel form a natural source of taxanes containing Paclitaxel to be extracted, said process comprising the following steps:

a) washing with deionized or pure water a raw material comprising Paclitaxel, said raw material coming from said natural source of taxanes, such a washing allowing removal of soluble impurities from said raw material;

b) extracting with an organic solvent a wet raw material comprising Paclitaxel from said washed raw material;

c) contacting said wet raw material with a salt to obtain a biomass by precipitation and isolating and drying said biomass;

d) removing resin and natural pigments from the so isolated and dried biomass by dissolving said biomass in acetone or an acetone-hexane mixture and then adding thereto at least one-polar solvent until a Paclitaxel-enriched oil phase is obtained;

e) chromatography purifying at least once the Paclitaxel-enriched oily phase obtained in the preceding step in a volatile solvent to obtain a purified solution and crystallization at least once the purified solution obtained by chromatography.

2. The process according to claim 1, where step e) comprises the following sub-steps:

$e_{-1}$) preparing a mixture of the Paclitaxel-enriched oil phase obtained in step (d) with silica gel, treating with an elution solvent said mixture in a chromatographic column comprising silica gel to obtain first Paclitaxel-enriched fractions;

$e_{-2}$) evaporating to dryness the first Paclitaxel-enriched fractions until a residue is obtained, preparing a mixture by solubilizing said residue in acetone and crystallizing the Paclitaxel contained in the mixture with a non-polar solvent, or evaporating the first Paclitaxel-enriched fractions until an acceptable concentration of Paclitaxel is obtained and crystallizing the Paclitaxel contained in the mixture with a non-polar solvent;

$e_{-3}$) solubilizing in acetone Paclitaxel crystals obtained in sub-step ($e_{-2}$) and recrystallizing the Paclitaxel with a non-polar solvent;

$e_{-4}$) solubilizing the crystals obtained in sub-step ($e_{-3}$) in a volatile solvent to obtain a solution, preparing a mixture of said solution with silica gel, and treating with an elution solvent said mixture in a chromatographic column comprising silica gel to obtain second Paclitaxel-enriched fractions with an elution solvent; and $e_{-5}$) evaporating to dryness the second Paclitaxel-enriched fractions obtained in sub-step ($e_{-4}$) until a residue is obtained, solubilizing the residue in a cetone, an alcohol, an ether, an ethyl acetate or a mixture thereof, and crystallizing Paclitaxel with a non-polar solvent.

3. The process according to claim 2, wherein the natural source of taxanes containing Paclitaxel consists of conifers selected from the group consisting of *Taxus brevifolia, Taxus baccata, Taxus canadensis, Taxus wal*(l)*ichiana, Taxus yunnanensis, Taxus densiformis, Taxus hicksii, Taxus wardii, Taxus cuspidata, Taxus capitata, Taxus brownii*.

4. The process according to claim 3, wherein:

in step (a), the raw material is selected from the group consisting of barks, branches and needles of said conifers, or mixtures thereof.

5. The process according to claim 4, wherein:

in step (b): the organic solvent is selected from the group consisting of alcohols or ketones and mixture of alcohol and ketone.

6. The process according to claim 5, wherein:

in step (b), the organic solvent is methanol, acetone or a mixture of methanol and acetone present in a volume ratio ranging from 9:1 to 1:9.

7. The process according to claim 4, wherein:

in step (c), the salt used to obtain the biomass by precipitating is selected from the group consisting of sodium chloride, ammonium chloride, ammonium sulfate, sodium acetate, potassium acetate and mixtures thereof.

8. The process according to claim 7, wherein:

in step (c), the salt is sodium chloride; the use in a concentration between 10 to 100 g per liter of the wet raw material extracted in step (b).

9. The process according to claim 7, wherein:

in step (c), the precipitated biomass is isolated by filtration or centrifugation, and then directed in air or by lyophilization.

10. The process according to claim 4, wherein:

in step (d), the dried biomass obtained in step (c) is dissolved by adding acetone and then water, the water being added at a ratio of 2 to 10 volumes per 100 volumes of acetone added, and wherein, in said step (d) said at least one non-polar solvent is selected from the group consisting of hexane and pentane.

11. The process according to claim 4, wherein:

in step ($e_{-1}$), the Paclitaxel-enriched oil phase obtained in step (d) is mixed with silica gel and dried in air; the silica gel is recovered and loaded into a chromatographic column also containing silica gel; and the Paclitaxel is then purified with an elution mixture containing from 30% to 40% acetone and from 60% to 70% hexane; and in step ($e_{-3}$), the crystals obtained in step ($e_{-2}$) are isolated by filtration or centrifugation and dissolved in acetone to form a solution, the volume of acetone being adjusted so as to obtain an absorbency of said solution having a value of 1.0 to 1.5 O.D. (optic density) for the peak corresponding to HPLC analysis, and the Paclitaxel is then recrystallized by adding from 3 to 4 volumes of hexane in the solution.

12. The process according to claim 11, wherein:

in step ($e_{-2}$), the enriched fractions containing Paclitaxel obtained by chromatography in step ($e_{-1}$) are grouped together, evaporated to dryness and dissolved in the acetone to form a solution, the amount of acetone being adjusted so as to obtain an absorbency of said solution having a value of 1.0 to 1.5 O.D. (optic density) for the peak corresponding to HPLC analysis; and the Paclitaxel is then crystallized by adding from 3 to 4 volumes of hexane in the solution.

13. The process according to claim 11, wherein:

in step ($e_{-2}$): the enriched fractions containing Paclitaxel obtained by chromatography in step ($e_{-1}$) are grouped together and evaporated until obtention an absorbency of said enriched fractions having a value of 1.0 to 1.5 O.D. (optic density) for the peak corresponding to HPLC analysis; and the Paclitaxel is then crystallized by adding from 1.5 to 2 volumes of hexane in the enriched solution.

14. The process according to claim 11, wherein:

in step ($e_{-4}$), the crystals obtained in step ($e_{-3}$) are filtered or centrifuged and dissolved in acetone to form a solution; the solution is then mixed with silica gel and dried under ventilation; the silica gel covered with Paclitaxel is loaded into a chromatographic column also containing silica gel; and the Paclitaxel is then repurified with an organic-solvent based elution mixture comprising from 30% to 40% acetone and from 60% to 70% hexane.

15. The process according to claim 11, wherein:

in step ($e_{-4}$), the crystals obtained in step ($e_{-3}$) are filtered or centrifuged and dissolved in acetone to form a solution; the solution is then mixed with silica gel and dried under ventilation; the silica gel covered with Paclitaxel is loaded into a chromatographic column also containing silica gel; and the Paclitaxel is then repurified with an organic-solvent based elution mixture comprising from 95% to 98% methylene chloride and from 2% to 5% isopropanol.

16. The process according to claim 11, wherein:

in step ($e_{-5}$), the enriched fractions containing Paclitaxel obtained by chromatography in step ($e_{-4}$) are combined according to their purity, evaporated to dryness and then dissolved in acetone to form a solution, the amount of acetone being adjusted so as to obtain an absorbency of said solution having a value of 1.0 to 1.5 O.D. (optic density) for the peak corresponding to HPLC analysis; and the Paclitaxel is then crystallized by adding from 3 to 4 volumes of hexane in the solution.

17. The process according to claim 11, wherein:

in step ($e_{-5}$), the enriched fractions containing Paclitaxel obtained by chromatography in step ($e_{-4}$) are grouped together and evaporated until obtention an absorbency of said enriched fractions having a value of 1.0 to 1.5 O.D. (optic density) for the peak corresponding to HPLC analysis; and the Paclitaxel is then crystallized by adding from 1.5 to 2 volumes of hexane in the enriched solution.

18. The process according to claim 11, wherein:

in step ($e_{-5}$), the enriched fractions containing Paclitaxel obtained by chromatography in step ($e_{-4}$) are combined according to their purity, evaporated to dryness and then dissolved in ethanol to form a solution, the amount of ethanol being adjusted so as to obtain a Paclitaxel concentration about 5 to 10 mg/ml of the solution according to HPLC analysis; and the Paclitaxel is then crystallized by adding from 3 to 4 volumes of hexane in the solution.

19. The process according to claim 11, wherein:

in step ($e_{-5}$), the enriched fractions containing Paclitaxel obtained by chromatography in step ($e_{-4}$) are combined according to their purity, evaporated to dryness and then dissolved in ethyl acetate to form a solution, the amount of ethyl acetate being adjusted so as to obtain a Paclitaxel concentration about 5 to 10 mg/ml of the solution according to HPLC analysis; and the Paclitaxel is then crystallized by adding from 3 to 4 volumes of hexane in the solution.

20. The process according to claim 11, wherein:

in step ($e_{-5}$), the enriched fractions containing Paclitaxel obtained by chromatography in step ($e_{-4}$) are combined according to their purity, evaporated to dryness and then dissolved in diethyl ethar to form a solution, the amount of diethyl ether being adjusted so as to obtain a Paclitaxel concentration about 5 to 10 mg/ml of the solution according to HPLC analysis; and the Paclitaxel is then crystallized by adding from 1 to 2 volumes of hexane in the solution.

21. The process according to claim 11, wherein:

in step ($e_{-3}$), the volatile solvent is selected from the group consisting of acetone, C1–C3 light alcohols, ethyl acetate, diethyl ether, methylene chloride and mixtures thereof.

22. The process according to claim 2, comprising the additional steps of:

extracting with methanol, crystals of 9-dihydro-13-acetylbaccatin III from the eluted fractions before isolation of Paclitaxel in step ($e_{-1}$) and from the mixtures obtained after crystallization in steps ($e_{-2}$) and ($e_{-3}$); and recrystallizing the so extracted crystals with a mixture of acetone-hexane.

* * * * *